United States Patent [19]

Degelaen et al.

[11] Patent Number: 4,546,076

[45] Date of Patent: Oct. 8, 1985

[54] ENZYMATIC PROCESS FOR THE DETERMINATION OF BETA-LACTAM ANTIBIOTICS

[75] Inventors: Jacques Degelaen, Genappe; Albert Loffet; Jean-Pierre Durieux, both of Braine-le-Chateau, all of Belgium

[73] Assignee: U C B Societe Anonyme, Brussels, Belgium

[21] Appl. No.: 462,233

[22] Filed: Jan. 31, 1983

[30] Foreign Application Priority Data

Feb. 1, 1982 [GB] United Kingdom ............... 8202790

[51] Int. Cl.$^4$ .............................................. C12Q 1/36
[52] U.S. Cl. ...................................... 435/24; 435/180
[58] Field of Search ................................ 435/24, 180

[56] References Cited

U.S. PATENT DOCUMENTS 4,170,696 10/1979 Hirohara et al. ................... 435/180

OTHER PUBLICATIONS

Fuad et al.—Biochem. J., vol. 155, (1976), pp. 623–629.
Frere et al., *Antimicrobial Agents and Chemotherapy*, vol. 18, No. 4, Oct. 1980, pp. 506–510.
*Chemical Abstracts*, vol. 90, No. 25, Jun. 18, 1979, p. 227, No. 199525M.
*Chemical Abstracts*, vol. 85, No. 23, Dec. 6, 1976, p. 180, No. 173261U.
*Chemical Abstracts*, vol. 87, No. 7, Aug. 15, 1977, p. 73, No. 48470b.
*Chemical Abstracts*, vol. 88, No. 5, Jan. 30, 1978, pp. 187–188, No. 33780Z.

*Primary Examiner*—Sam Rosen
*Attorney, Agent, or Firm*—Wenderoth, Lind & Ponack

[57] ABSTRACT

An enzymatic process for the determination of beta-lactam antibiotics in a biological liquid, comprising the steps of: (1) incubating the liquid with soluble D-alanyl-D-alanine-carboxypeptidase produced by Actinomadura R 39, said enzyme being immobilized on a water-insoluble support, the beta-lactam antibiotic reacting with the immobilized enzyme to form an inactive and equimolecular enzyme-antibiotic complex; (2) separating the immobilized enzyme from the liquid and washing it; (3) incubating the immobilized enzyme with a substrate solution to hydrolyze it and form an amount of D-alanine corresponding to the residual enzymatic activity; (4) determining the amount of D-alanine formed; and (5) comparing the determination of step (4) with a standard to obtain the concentration of the antibiotic in the biological liquid; as well as a test set for carrying out this process and comprising the necessary reagents.

17 Claims, 1 Drawing Figure

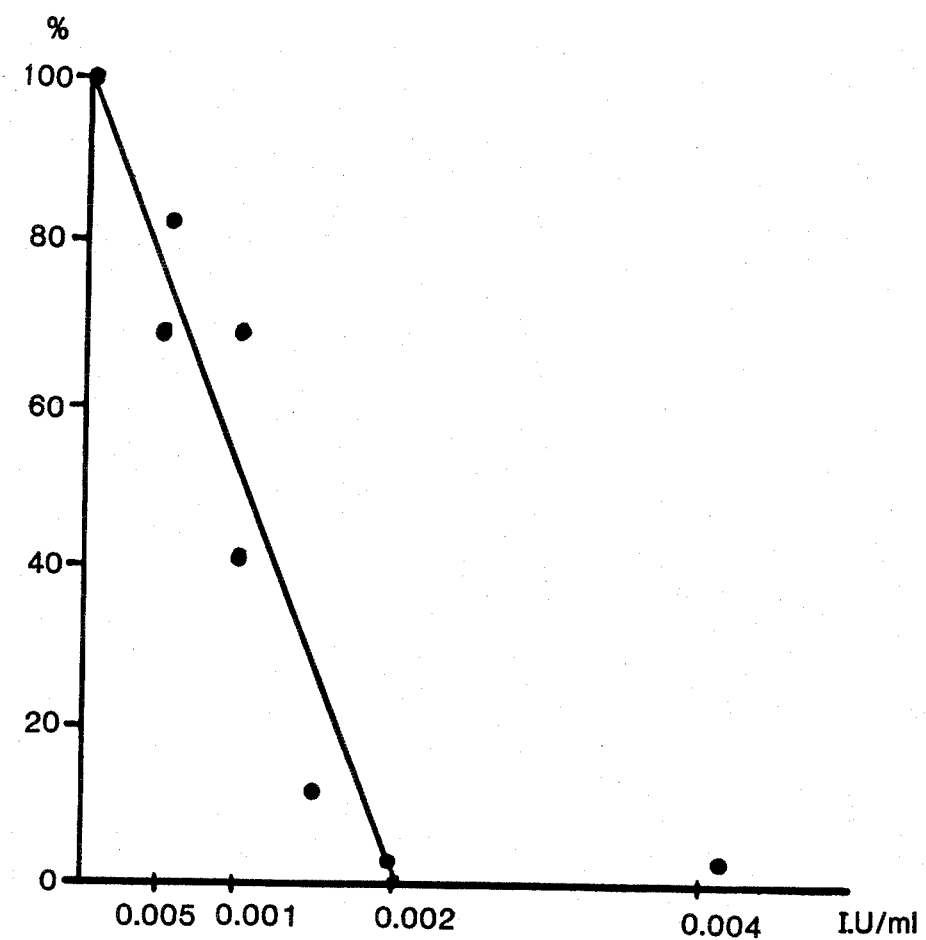

ENZYMATIC PROCESS FOR THE DETERMINATION OF BETA-LACTAM ANTIBIOTICS

The present invention relates to a rapid and sensitive enzymatic process for the determination of beta-lactam antibiotics in a biological liquid, such as milk, urine and blood serum. It also procures a test set which can be used by carrying out this process.

At the present time, antibiotics are very widely used not only as therapeutic agents in the treatment of infectious diseases caused by bacteria but also as preservatives for foodstuffs and as additives in animal feed for stimulating growth. There is, therefore, an ever-increasing need to be able to detect the presence of antibiotics, even in very low concentrations, in complex biological liquids, such as milk, urine, blood, serum, saliva, meat extracts and fermentation liquids.

The case of milk production is an example of this. In fact, it is well known to use penicillins for treating certain infectious diseases of milk-producing live-stock, for example mastitis. However, for obvious medical reasons, milk intended for human consumption must, in principle, be free of any trace of antibiotics. Furthermore, concentrations of penicillin of 0.005 I.U./ml or less can have adverse effects during the manufacture of products derived from milk, such as cheese, yogurt and the like.

Therefore, it is necessary to be able to determine, rapidly and accurately, the concentration of penicillins in the milk produced by live-stock and preferably to be able to do this directly on site at the farm.

Microbiological processes which make it possible to determine relatively low concentrations of beta-lactam antibiotics in biological liquids have existed for a long time. These processes are based on the measurement of the inhibition of the growth of microorganisms sensitive to antibiotics in the presence of a sample of the biological liquid. However, these processes require a considerable amount of time and a high level of technical skill; in the best case, the time required to obtain a result is about 2 to 3 hours, which is not admissible in practice.

More recently, a rapid microbiological process for detecting the presence of antibiotics in a biological liquid, in particular in milk, has also been proposed (cf. U.S. Pat. No. 4,239,852).

According to this method, the sample of liquid to be examined is incubated, on the one hand, with cells or cell parts of a micro-organism which is very sensitive to antibiotics, in particular *Bacillus stearothermophilus*, and, on the other hand, with an antibiotic tagged with a radioactive element or with an enzyme. During the incubation, the antibiotic, if present in the sample, and the tagged antibiotic compete to attach themselves to the receptor sites of the cells or cell parts. The amount of tagged antibiotic which has been attached to the cells or cell parts is then determined. This provides an indication of the presence (or absence) of antibiotics, since the amount of tagged antibiotic attached is inversely proportional to the concentration of antibiotic in the sample.

According to this U.S. Patent Specification, this process makes it possible to detect antibiotic concentrations as low as 0.01 I.U./ml or even as 0.001 I.U./ml in milk, in a little less than 15 minutes.

However, the major disadvantage of this process is the fact that, to achieve this result, the use of an antibiotic tagged with a radioactive element ($^{14}C$ or $^{125}I$) is compulsory and this must be determined with the aid of a special instrument, for example, a scintillation counter. Furthermore, the handling of radioactive materials, even in very small amounts, is not totally without danger for the person performing the analysis.

It is true that, in Example 2 of this U.S. Patent Specification, another embodiment of this process is described in which an enzyme-tagged antibiotic is used and in which the amount of tagged antibiotic is determined by a visual colorimetric method. However, this variant only makes it possible to detect whether there is more (or less) than 0.05 I.U./ml of penicillin in a milk sample. This process is, therefore, distinctly less sensitive and, consequently, much less useful.

A recent article describes an enzymatic process which makes it possible to determine low concentrations of beta-lactam antibiotics in human sera and in milk (J.-M. FRERE, D. KLEIN and J.-M. GHUYSEN, *Antimicrobial Agents and Chemotherapy*, 18 (1980, No. 4), 506–510.

This process (designated hereinafter as the "J.-M. FRERE process") is much more valuable because it does not necessitate the use of radioactive materials requiring sophisticated measuring instruments and is at the same time very rapid and remarkably precise. This process is based upon the use of a specific enzyme, i.e. the soluble exocellular D-alanyl-D-alanine-carboxypeptidase, which is produced by Actinomadura R 39 (previously called Streptomyces R 39). In the present specification, this enzyme is designated "enzyme R 39". As its name indicates, enzyme R 39 possesses a specific activity for the hydrolysis of the D-alanyl-D-alanine end groups of various peptides. By way of example, the tripeptide $N^{alpha}$, $N^{epsilon}$-diacetyl-L-lysyl-D-alanyl-D-alanine undergoes a hydrolysis reaction, under the catalytic influence of enzyme R 39, according to the equation:

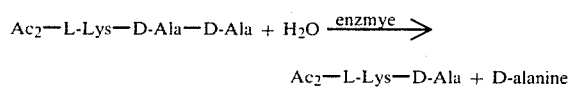

$$Ac_2-L-Lys-D-Ala + D-alanine$$

Another important characteristic of enzyme R 39 is the fact that it reacts with beta-lactam antibiotics to form, very rapidly, an equimolecular enzyme-antibiotic complex which is inactive and substantially irreversible.

In the J.-M. FRERE process, these properties of enzyme R 39 are used to determine very low concentrations of beta-lactam antibiotics. This process comprises three essential steps. In a first step, a definite volume of a sample of the liquid to be examined is incubated with a definite amount of enzyme R 39. The incubation is conducted under conditions allowing the beta-lactam antibiotic, if present in the sample, to react with the enzyme to form an inactive and substantially irreversible equimolecular enzyme-antibiotic complex.

In a second step, a definite amount of substrate, for example $N^{alpha}$, $N^{epsilon}$-diacetyl-L-lysyl-D-alanyl-D-alanine, is incubated with the product obtained in the first step, under conditions allowing the substrate to be hydrolyzed by the enzyme to form an amount of D-alanine corresponding to the residual enzymatic activity of the enzyme R 39 which has not been complexed with the antibiotic in the first step.

In a third step, the amount of D-alanine thus formed is determined. Those skilled in the art will easily understand that, according to the amount of antibiotic present in the sample, a corresponding amount of enzyme R 39 will be inactivated in the first stage and that the amount of D-alanine formed in the second stage (which obviously depends on the residual activity of the enzyme) is, therefore, inversely proportional to the amount of antibiotic present in the sample. If, for example, the sample is free of antibiotic, the enzyme R 39 is not inactivated and the amount of D-alanine found corresponds to the total activity of the enzyme R 39 used. On the other hand, if the sample contains a molar amount of antibiotic which is equal to or greater than the molar amount of enzyme R 39 used, the latter is completely inactivated by the antibiotic and no D-alanine is formed. Between these two extreme situations, the amount of D-alanine found corresponds to the percentage residual activity of the enzyme R 39. In other words, the amount of D-alanine formed provides a precise quantitative indication of the concentration of antibiotic present in the sample subjected to examination.

In the J-M. FRERE process, this amount of D-alanine is determined by an enzymatic method. This is based on two coupled enzymatic reactions. In the first reaction, the D-alanine is oxidized to pyruvic acid with the aid of a D-amino acid oxidase (together with its co-enzyme, flavin-adenine dinucleotide); a corresponding amount of hydrogen peroxide is formed at the same time from the oxygen in the air. In the second reaction, the hydrogen peroxide formed is used to oxidize o-dianisidine with the aid of a peroxidase.

It is for this reason that, in the third step of the J-M. FRERE process, the mixture obtained in the second step is incubated with a set of reagents comprising a D-amino acid oxidase, its coenzyme (flavin-adenine dinucleotide (FAD)), a peroxidase and o-dianisidine. As the oxidized form of o-dianisidine is colored, a brown coloration is produced at the end of this incubation, the intensity of the coloration being a function of the amount of D-alanine.

This, therefore, makes it possible to determine the amount of D-alanine by a colorimetric method, either visually or by measuring the optical density on a spectrophotometer ($\lambda max = 460$ nm).

By preparing a series of samples with a known antibiotic concentration and by applying this process, it is thus possible to plot a standard curve which relates the percentage residual enzymatic activity of the enzyme R 39 to the antibiotic concentration.

To obtain a quantitative indication of the antibiotic concentration in a sample, exactly the same procedure is then followed and the antibiotic concentration is determined by referring to this standard curve. This quantitative evaluation obviously requires the use of a spectrophotometer.

However, to determine whether or not the concentration of antibiotic exceeds a certain critical value, it is not necessary to use a spectrophotometer or other similar measuring instrument. It suffices to know beforehand the critical antibiotic concentration at which the activity of the enzyme R 39 is totally suppressed or, in other words, the antibiotic concentration at which no D-alanine is formed and, consequently, no coloration is produced at the and of the final incubation. With a knowledge of this critical concentration, it is obvious that it is possible, by means of a simple visual inspection of the result of the determination, to judge whether or not a given sample contains a lower or higher concentration of antibiotic than the said critical concentration.

It is, therefore, apparent that, by this process, an indication of the concentration of antibiotic in milk can be obtained rapidly and accurately without using a special instrument.

Furthermore, this process makes it possible to determine relatively low concentrations of beta-lactam antibiotic in milk and in human sera. Thus, for example, starting from milk samples having a volume of about 20 $\mu l$ and incubating them with 3 picomols of enzyme R 39, it is possible to determine, quantitatively (using a spectrophotometer), concentrations of penicillin as low as 0.02 I.U./ml of milk, and qualitatively, by the visual method described above, concentrations of more than 0.09 I.U./ml of milk, in less than one hour.

However, the J-M. FRERE process has several serious drawbacks.

First, for the determination of antibiotics in biological liquids, such as milk and serum, it is absolutely necessary first to remove the substances, which disturb the colorimetric determination, from the samples subjected to the determination. In the case of milk, for example, it is necessary first to precipitate the proteins with citric acid or rennet and then to filter the sample treated in this way so as to obtain a clear filtrate which can no longer disturb the colorimetric determination. This operation of precipitating the proteins is complicated and tedious, which means that the process cannot easily be carried out at the site of milk production by unskilled persons.

Secondly, the sensitivity of the J-M. FRERE process, in particular in the case of biological liquids (milk, saliva, serum and the like), is insufficient. It is true that this sensitivity could be increased by reducing the amount of enzyme R 39 used. In fact, if 0.3 picomole of enzyme were used instead of 3 picomols, for example, it would theoretically be possible to determine concentrations of antibiotic which are ten times lower. However, when the amount of enzyme is reduced, it is also necessary to increase, in the same proportions, on the one hand, the time of reaction between the antibiotic and the enzyme R 39 and, on the other hand, the hydrolysis time of the substrate. This means that both the first and the second steps of the process take about ten times longer.

One of the prime advantages of the J-M. FRERE process, namely its rapidity, would thus be lost and this is inadmissible.

Furthermore, attempts could also be made to increase the sensitivity by increasing the volume of the sample which must be incubated with the enzyme R 39. In fact, if a sample having a volume of 200 $\mu l$ instead of 20 $\mu l$ were used, for example, it would theoretically be possible to determine concentrations of antibiotic which are ten times lower. Furthermore, in this case, it would only be necessary to increase the time of reaction between the antibiotic and the enzyme R 39, i.e. only the duration of the first step of the process.

Unfortunately, it is not possible to increase the sensitivity of the J-M. FRERE process in this way, in particular in the case of complex liquids of biological origin. In fact, it has been found that it is impossible to carry out a suitable determination if the volume of the sample of biological liquid exceeds a certain critical volume, which varies according to the nature of the biological liquid. Thus, in the case of milk, if the sample volume which is subjected to incubation exceeds about 20 $\mu l$, it is observed that the amount of oxidized o-dianisidine formed is greatly reduced. The same applies to serum if the sample volume incubated with the enzyme R 39 exceeds about 50 μl.

Finally, in the case of urine, no enzymatic activity is detected, even using sample volumes as low as 10 μl. It is, therefore, impossible to use this process for the determination of antibiotics in urine.

It is assumed that biological liquids contain substances which inhibit the action of the enzymes used in the process; it is thus impossible to use large sample volumes.

It is for this reason that we have developed a new enzymatic process for the determination of beta-lactam antibiotics in a biological liquid, which process is further improved in that it does not have the various drawbacks of the prior art processes.

We have now found that it is possible to overcome the various drawbacks of the J-M. FRERE process by immobilizing the enzyme R 39 on a water-insoluble support, in particular on a poly(N,N-dimethylacrylamide) resin.

Therefore, the present invention provides an improved enzymatic process for the determination of beta-lactam antibiotics in a biological liquid, which process comprises the steps of:

(1) incubating the liquid with the soluble D-alanyl-D-alanine-carboxypeptidase produced by Actinomadura R 39, said enzyme being immobilized on a water-insoluble support, said incubation being conducted under conditions allowing the beta-lactam antibiotic, if present in said liquid, to react with the enzyme to form an inactive and substantially irreversible equimolecular enzyme-antibiotic complex;

(2) separating the immobilized enzyme from the liquid and washing it;

(3) incubating the immobilized enzyme of step (2) with a substrate solution under conditions allowing the substrate to be hydrolyzed by the enzyme to form an amount of D-alanine corresponding to the residual enzymatic activity;

(4) determining the amount of D-alanine formed in step (3); and (5) comparing the determination of step (4) with a standard to obtain the concentration of the antibiotic in the biological liquid.

In contrast to the J-M. FRERE process, the process according to the present invention makes it possible to carry out a determination directly on the biological liquid as such. It is not necessary for the substances which are capable of disturbing the colorimetric determination to be removed beforehand from the samples subjected to the determination.

In fact, as the enzyme R 39 is immobilized on a water-insoluble support, after it has reacted with the antibiotic (if present in the biological liquid), this immobilized enzyme can easily be separated from the biological liquid by simple filtration and washed. Consequently, during the subsequent operations, there is no longer any possibility of interference by the biological liquid because it has already been removed at step (2) of the process.

One of the major disadvantages of the J-M. FRERE process is thus overcome.

Surprisingly, we have also found that, by applying the process according to the present invention, it is possible to carry out excellent determinations on sample volumes of biological liquid of between 200 μl and 5 ml without the slightest difficulty.

This is of fundamental importance. In fact, as explained above, by increasing the sample volume which must be incubated with the enzyme R 39, it is possible to increase the sensitivity of the process. As already explained, one of the drawbacks of the J-M. FRERE process is the fact that it is not possible to exceed a critical volume (of the order of 20 μl for milk and 50 μl for serum). As this drawback is eliminated by the process according to the present invention, it is obvious that, in contradistinction to the J-M. FRERE process, the process of the present invention makes it possible to obtain a much greater sensitivity in the determination of biological liquids, such as milk, serum and the like. As will be shown hereinafter in the Examples, the process according to the present invention thus makes it possible, starting from 1 ml samples of milk, to determine visually and with certainty concentrations of penicillin G of more than 0.002 I.U./ml (1.2 ng/ml) of milk and, with the aid of a spectrophotometer, concentrations as low as 0.0005 I.U./ml (0.3 ng/ml) of milk, in a time of less than one hour. By way of comparison, it is recalled that the process described in U.S. Pat. No. 4,239,852 makes it possible to detect concentrations of the order of 0.01 to 0.001 I.U./ml of milk, provided, however, that radioactive materials and a scintillation counter are used.

We have also found that the process according to the present invention can be applied successfully to the determination of antibiotics not only in milk and serum but also in other complex biological liquids, for example urine, blood, saliva, meat extracts and fermentation liquids. Seen in this light, the process of the present invention represents a considerable advance compared with the J-M. FRERE process.

The prime advantage of the process of the present invention is, therefore, that it makes it possible rapidly to detect very low concentrations of beta-lactam antibiotics for example of the order of 0.002 I.U./ml, in the widest variety of biological liquids, without having to use a special analytical instrument.

The antibiotics, the concentration of which can be determined using the process according to the present invention belong to the group of antibiotics which are characterized by the presence of a beta-lactam ring in their molecule, i.e. in principle all the penicillins and cephalosporins. Examples of penicillins which may be mentioned include benzylpenicillin (penicillin G), ampicillin, phenoxymethylpenicillin, carbenicillin, methicillin, oxacillin, cloxacillin and the like and examples of cephalosporins which may be mentioned include cephalosporin C, cephaloglycin, cephalothin, cephalexin and the like. Particularly favorable results have been obtained with penicillin G.

In step (1) of the process according to the present invention, a definite volume of a sample of the biological liquid is incubated with a definite amount of enzyme R 39, immobilized on a water-insoluble support.

As explained above, because the enzyme R 39 is immobilized on a water-insoluble support, it is possible to work with very large sample volumes. By increasing the sample volume, the sensitivity of the process is increased accordingly. For example, by doubling the volume of the sample, the sensitivity is doubled, by tripling the volume of the sample, the sensitivity is tripled and so on. It is, therefore, possible to choose the volume of the sample according to the desired sensitivity. In the case of milk, for example, the sensitivity of the process can be adapted to the standards fixed by the legislation of the country in which it is used or to the requirements of the dairy industry.

It is true that the same effect can also be obtained by reducing the amount of enzyme R 39. However, in this case, not only the duration of step (1) but also the duration of step (3) of the process must be increased proportionally, whereas, by increasing the sample volume only the duration of step (1) of the process is affected. It is, therefore, preferable to work with a constant amount of enzyme R 39, for example an amount of about 3 picomols, and to adapt the sample volume to the desired sensitivity, according to circumstances.

In practice, sample volumes of between 200 μl and 5 ml are used, which allow the determination of very low concentrations of antibiotic, for example of the order of 0.002 I.U./ml of penicillin, in an hour or less. The excellent sensitivity, the rapidity and the precision of the process according to the present invention result from the particular characteristics of enzyme R 39, on the one hand, and from its immobilization on a water-insoluble support, on the other hand.

In fact, enzyme R 39 is characterised by:
the extremely rapid formation of an inactive equimolecular enzyme-antibiotic complex;
the extraordinary stability of the said complex, because, once formed, it only breaks down very slowly (by way of example, the half-life of the complex formed between enzyme R 39 and penicillin G is about 70 hours at 37° C.); and
an excellent enzymatic activity resulting in very rapid hydrolysis of the D-alanyl-D-alanine end groups of the peptide substrate.

By virtue of these three characteristics, enzyme R 39 occupies a unique position compared with the D-alanyl-D-alanine-carboxypeptidases identified up to the present. In fact, since the time of break down of the enzyme-antibiotic complex is infinitely longer than the total time which is necessary, respectively, for forming the complex and for measuring the residual enzymatic activity, there is no danger that the results of the determination will be altered by the release of active enzyme due to premature break down of the enzyme-antibiotic complex.

If the presently known D-alanyl-D-alanine-carboxypeptidases are examined, enzyme R 39 is the only one which perfectly satisfies these conditions; in fact, either the rate of formation of the complex is about ten times slower or the stability of the antibiotic-enzyme complex is completely insufficient or the hydrolysis rate of the peptide substrate is much too slow (this is the case, in particular, with all the membrane-bound endocellular carboxypeptidases).

Enzyme R 39 is the specific, soluble exocellular D-alanyl-D-alanine-carboxypeptidase which is excreted by Actinomadura R 39 when this microorganism (deposited on July 10, 1981, at the Institut Pasteur in Paris, under No. I-127) is cultivated in an appropriate culture medium.

To carry out the process of the present invention, this enzyme must obviously be substantially pure. Its preparation and its purification can be carried out according to the methods described in the literature (in this connection, see the article by J-M. FRERE et al., Biochem.J. 143,(1974),233-240 entitled "Molecular Weight, Amino Acid Composition and Physicochemical Properties of the Exocellular DD-Carboxypeptidase-Transpeptidase of Streptomyces R 39"). However, this enzyme is now commercially available in the pure state; it can be obtained from UCB BIOPRODUCTS, S.A. (Belgium).

According to the present invention, the soluble enzyme R 39 is immobilized on a water-insoluble support.

The method used for this immobilization is not critical. All the conventional methods known to those skilled in the art can, therefore, be used for this purpose; amongst these methods, those which involve either attachment of the enzyme to the support by a covalent bond or physical adsorption of the enzyme to the support or entrapping the enzyme in a polymer matrix, may be particularly mentioned.

The nature of the support material is also not critical. In principle, it is possible to use any organic or inorganic water-insoluble material commonly employed for the immobilization of an enzyme. Appropriate support materials which may be mentioned include natural polymers, such as cellulose and its derivatives, agarose, starch and its derivatives, dextran, collagen, keratin and the like; synthetic polymers, such as cross-linked polyacrylamides in the form of beads or gels; cross-linked polystyrenes; ethylene-maleic anhydride copolymers; polyamides; cross-linked poly(2-hydroxyethyl methacrylate); ion exchange resins and the like; and inorganic substances, such as glass, alumina, silica, calcium carbonate, hydroxyapatite, clays and the like.

However, those skilled in the art will understand that it is necessary to choose a method of immobilization which leaves all the properties of enzyme R 39 intact and which in no way affects its enzymatic activity, even after a prolonged period of storage.

A support material which is particularly preferred for carrying out the process according to the present invention is cross-linked poly(N,N-dimethylacrylamide) resin, the use of which has already been proposed in the synthesis of polypeptides in the solid phase (cf. R. AR-SHADY et al., J.Chem.Soc.Chem.Commun.1979,No.9, 423-425). This resin has the advantage that it can easily be swollen in a wide variety of both organic and aqueous solvents (water, methanol, N,N-dimethylformamide, N,N-dimethylacetamide, pyridine or dichloromethane) and also that it can be handled easily. It is preferably prepared by the emulsion copolymerization of a mixture of N,N-dimethyl-acrylamide, N,N'-ethylene-bis-acrylamide and the methyl ester of N-acryloylsarcosine.

Under these conditions, the resin obtained is in the form of solid particles, for example spheres or beads, the size of which is preferably between 0.1 mm and 2 mm, and can, therefore, easily be filtered off.

This resin possesses a three-dimensional cross-linked structure, since the polymer chains are bound to one another by the N,N-ethylene-bis-acrylamide (which acts as a cross-linking agent) and it also carries ester groups because of the introduction of the methyl ester of N-acryloylsarcosine ($CH_2=CH-CO-N(CH_3)-CH_2-COOCH_3$) into the polymer chains.

When the polymerisation of this resin has ended, the ester groups carried by this resin are also converted to functional amino groups by reaction with ethylenediamine, according to the equation:

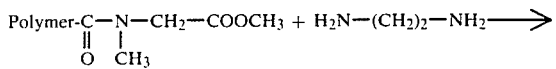

-continued
$$\text{Polymer-C-N-CH}_2\text{-CO-HN-(CH}_2)_2\text{-NH}_2$$
$$\overset{\|}{O} \overset{|}{CH_3}$$

groups, introduced into this resin by the N-hydroxysuccinimide ester, with the free amino groups of the enzyme R 39, according to the equation:

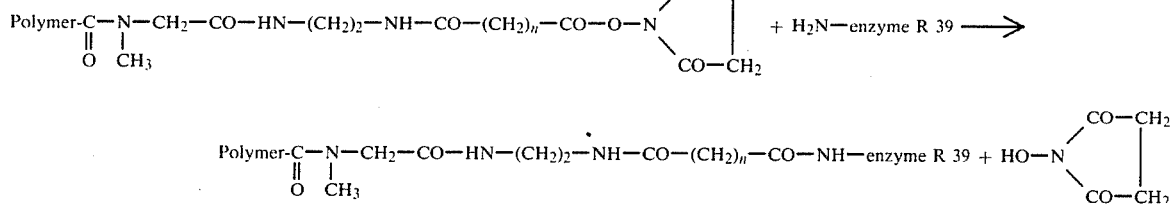

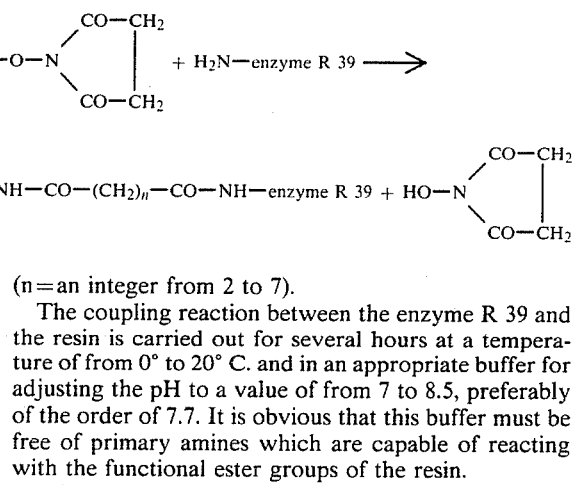

($n$=an integer from 2 to 7).

The coupling reaction between the enzyme R 39 and the resin is carried out for several hours at a temperature of from 0° to 20° C. and in an appropriate buffer for adjusting the pH to a value of from 7 to 8.5, preferably of the order of 7.7. It is obvious that this buffer must be free of primary amines which are capable of reacting with the functional ester groups of the resin.

When the coupling reaction has ended, the unreacted ester groups are blocked by the amino groups of compounds such as ethanolamine or the methyl ester of glycine. The immobilized enzyme thus obtained is washed with an appropriate buffer and can be used as such for carrying out the process according to the present invention.

Using this method, the yields of the immobilization are excellent; they can vary between 15 and 95%, depending upon the pH of the buffer used and also upon the duration and temperature of the coupling reaction.

A detailed example, illustrating this method of immobilization of enzyme R 39 on a poly(N,N-dimethylacrylamide) resin, is given below:

The poly(N,N-dimethylacrylamide) modified in this way generally contains from 0.2 to 1 millimole of ethylene-diamine per gram of resin. In this form, it constitutes an ideal support material for the immobilization of enzyme R 39.

This immobilization is preferably carried out by attaching the enzyme R 39 to the resin by a covalent bond. In fact, in contrast to the other methods of immobilization, this method makes it possible to prevent the enzyme from leaching out from the support.

The covalent bonding of the enzyme R 39 to the poly(N,N-dimethylacrylamide) resin, modified with ethylenediamine in the manner just explained above, can be carried out, for example, by means of an appropriate coupling agent containing a functional group which can react with the functional amino groups of the poly(N,N-dimethylacrylamide) resin and another functional group which can react with the free amino groups of the enzyme R 39.

It is preferred to use coupling agents which contain ester groups having a sufficiently long half-life in an aqueous medium, for example, the N-hydroxysuccinimide diesters of an aliphatic dicarboxylic acid containing 4 to 9 carbon atoms, such as glutaric acid, suberic acid or the like. Indeed, since the coupling reaction with the free amino groups of the enzyme R 39 is carried out in an aqueous medium, the functional groups of the coupling agent must be sufficiently stable in this medium.

To attach the enzyme R 39 to the poly(N,N-dimethylacrylamide) resin modified by ethylenediamine, this resin is first reacted with an N-hydroxysuccinimide diester, in an appropriate organic solvent (for example N,N-dimethylacetamide) to prevent the hydrolysis of the ester groups. By means of this reaction, the functional amino groups of the resin are converted to functional ester groups according to the equation:

IMMOBILIZATION OF ENZYME R 39 ON A POLY(N,N-DIMETHYLACRYLAMIDE) RESIN (a) Preparation of the poly(N,N-dimethylacrylamide) resin carrying functional amino groups derived from ethylenediamine The poly(N,N-dimethylacrylamide) resin used as the support has been prepared by the emulsion copolymerisation of a mixture of N,N-dimethylacrylamide (12 g), N,N'-ethylenebisacrylamide (1 g) and the methyl ester of N-acryloylsarcosine (1.4 g), according to the method described by R. ARSHADY et al. (*J.Chem.Soc.Chem.-Commun.* 1979,No.9,423–425). This yields about 12 to 13 g of resin in the form of beads having a size of from 0.1 mm to 2 mm.

10 g of this resin are added to 320 ml of ethylenedi-

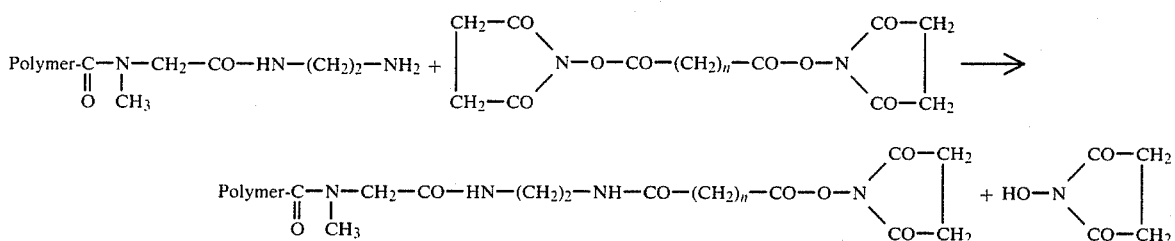

($n$=an integer from 2 to 7).

The coupling between the enzyme R 39 and the resin is then carried out by reacting the functional ester amine and the mixture obtained is stirred overnight at ambient temperature. The resin is then filtered off and washed successively with N,N-dimethylformamide and water until the filtrate has a neutral pH. Finally, the resin is washed with methanol and left in diethyl ether to reverse the swelling. This yields 10 g of resin containing 0.3 millimole of ethylenediamine per gram.

(b) Preparation of the poly(N,N-dimethylacrylamide) resin carrying functional ester groups derived from the N-hydroxysuccinimide diester of glutaric acid (b.1) Preparation of the N-hydroxysuccinimide diester of glutaric acid.

6.7 g of glutaric acid and 12.7 g of N-hydroxysuccinimide are dissolved in 50 ml of N,N-dimethylacetamide at 0° C. A solution of 23.7 g of dicyclohexylcarbodiimide in 50 ml of methylene chloride is added dropwise thereto. The reaction mixture is left to return to ambient temperature and, after standing overnight, it is filtered off and the filtrate is evaporated. The residue is recrystallized from diethyl ether. This gives the N-hydroxysuccinimide diester of glutaric acid with a virtually quantitative yield.

(b.2) Preparation of the poly(N,N-dimethylacrylamide) resin carrying functional ester groups.

500 mg of poly(N,N-dimethylacrylamide) resin carrying functional amino groups derived from ethylenediamine, prepared as described under a), are suspended in 50 ml of N,N-dimethylacetamide. 2 g of the N-hydroxysuccinimide diester of glutaric acid (prepared as described under b.1)) are added thereto. The mixture obtained is stirred for 24 hours at ambient temperature. The completion of the reaction is confirmed by the test of E. KAISER (*Anal.Biochem.* 34, (1970,No.2),595–8). The resin is filtered off and washed five times with 100 ml of N,N-dimethylacetamide and five times with 100 ml of methanol and the resin is then left in diethyl ether to reverse the swelling.

(c) Immobilization of the enzyme R 39 on the poly(N,N-dimethylacrylamide) resin carrying functional ester groups derived from the N-hydroxysuccinimide diester of glutaric acid (c.1) Preparation of the enzyme R 39.

The enzyme R 39 used has been prepared and purified according to the method described in the article by J-M. FRERE et al. (*Biochem.J.* 143, (1974),233–240).

The enzyme R 39 purified in this way possesses a specific activity of 19.8 units/mg of protein. One unit of enzyme R 39 catalyzes the hydrolysis of 1 $\mu$mol of $N^{alpha}$, $N^{epsilon}$-diacetyl-L-lysyl-D-alanyl-D-alanine per minute at 37° C., when the enzyme is incubated with an 8 mM solution of this substrate in a 0.03M Tris-HCl buffer (pH 7.5) supplemented with 3 mM $MgCl_2$.

600 $\mu$g of purified enzyme R 39, dissolved in 1 ml of 0.1M Tris-HCl buffer (pH 7.7) containing 0.2M NaCl and 0.05M $MgCl_2$, are subjected to dialysis for 6 hours against 200 ml of 0.1M Hepes buffer (pH 7.7) containing 0.1M NaCl and 0.05M $MgCl_2$. This operation is repeated four times.

Tris-HCl=2-amino-2-hydroxymethyl-1,3-propanediol-hydrochloride;
Hepes=4-hydroxyethyl-1-piperazineethanesulfonic acid.
M=mole per liter.

(c.2) Preparation of the resin.

100 mg of poly(N,N-dimethylacrylamide) resin carrying functional ester groups derived from the N-hydroxysuccinimide diester of glutaric acid, prepared as described under (b.2), are left to swell in 50 ml of N,N-dimethylacetamide. When the beads have reached their maximum swelling point (after about 3 hours), the resin is filtered off and washed five times with 100 ml of 0.1M Hepes buffer (pH 7.7) and five times with 100 ml of 0.1M Hepes buffer (pH 7.7) containing 0.1M NaCl and 0.05M $MgCl_2$.

(c.3) Coupling between the enzyme R 39 and the resin.

The moist resin, prepared as described under (c.2), is placed in a 10 ml vial. 70 $\mu$g (1,320 picomols) of enzyme R 39, prepared as described under lc.1) and dissolved in 1.75 ml of 0.1M Hepes buffer (pH 7.7) containing 0.1M NaCl and 0.05M $MgCl_2$, are added thereto. The vial is then rotated at 100 rpm for 16 hours at ambient temperature.

The resin is filtered off and washed five times with 10 ml of 0.1M Hepes buffer (pH 7.7) containing 0.1M NaCl and 0.05M $MgCl_2$.

After this operation, a waterpump vacuum is applied to the resin for 30 minutes.

The weight of the resin thus obtained is 503 mg. The enzymatic activity of the enzyme R 39 immobilized on this resin corresponds to 15 $\mu$g (283 picomols). The yield of the immobilization is therefore 21%.

Enzyme R 39 immobilized on a solid support possesses an excellent stability and, consequently, it withstands high temperatures which can range up to 70° C. It is for this reason that the incubation of the biological liquid with the immobilized enzyme R 39 can be carried out within a temperature range of from 20° to 50° C. Preferably, the temperature used is of the order of 37° C. Indeed, under these conditions, the incubation time, which is closely related to the time required for the formation of the inactive equimolecular enzyme-antibiotic complex, is about 20 minutes. Increasing the incubation temperature will have the effect of reducing the incubation time and vice versa. It is, therefore, possible to shorten the duration of the process even further by increasing the temperature.

According to the present invention, at the end of step (1) of the process, i.e. in step (2), the immobilized enzyme R 39 is separated from the biological liquid. This separation can be carried out by any appropriate method, for example by decantation, filtration or centrifugation, a simple filtration being preferred. The immobilized enzyme is then washed one or more times with an appropriate buffer in order to remove the traces of biological liquid which could still be present therein.

In step (3) of the process according to the present invention, the immobilized enzyme (from which the biological liquid has been removed) is incubated with a definite amount of substrate in solution.

During this step, the fraction of the enzyme which has not been consumed in the formation of the enzyme-antibiotic complex in step (1) of the process is used to hydrolyze a substrate specific to enzyme R 39. This hydrolysis reaction will, therefore, produce an amount of D-alanine corresponding to the residual activity of the enzyme R 39.

In view of the very nature of enzyme R 39, it is obvious that it will be possible to use, as the substrate, any peptide which possesses D-alanyl-D-alanine end groups. $N^{alpha}$, $N^{epsilon}$-diacetyl-L-lysyl-D-alanyl-D-alanine, $N^{alpha}$-acetyl-L-lysyl-D-alanyl-D-alanine and the like may be mentioned solely by way of non-limiting examples.

The amount of substrate used is not critical, provided that the amount of substrate used is in large excess relative to the amount of enzyme R 39 used. In fact, it is always necessary to operate under conditions of enzyme saturation by the substrate.

The operating conditions to be observed during this step are substantially the same as those indicated above for step (1). The incubation can be carried out within a temperature range of from 20° to 50° C. and preferably at a temperature of the order of 37° C. The incubation time must be at least sufficient to obtain a measurable amount of D-alanine with the non-inactivated enzyme R 39. This time is preferably about 30 minutes for an incubation temperature of 37° C. This time can be reduced by increasing the incubation temperature or, conversely, it can be increased by reducing the incubation temperature. Therefore, it is also advantageous to increase the temperature of this incubation in all cases where the rapidity of the determination is an important factor.

In order to preserve an optimum enzymatic activity, the incubation medium should preferably have a pH value of from 7 to 8.5. Usually, a pH value of the order of 7.7 is maintained by carrying out the incubation in an appropriate buffer.

In step (4) of the process according to the present invention, the amount of D-alanine formed in step (3) is determined.

This determination of the D-alanine can be carried out by chemical or enzymatic methods well known to those skilled in the art. It is important only that it should be rapid and inexpensive and that it should make it possible to determine D-alanine specifically, to the exclusion of all the other products which are present in the liquid to be examined.

It is for this reason that the enzymatic methods which permit a colorimetric determination of the D-alanine are the preferred methods.

A particularly preferred method is the enzymatic method described by J-M. FRERE et al. in "Methods in Enzymology, Volume XLV, part B (1976), 610–636", more particularly on pages 612 and 613.

In this method, the D-alanine is oxidized to pyruvic acid with the aid of a D-amino acid oxidase (together with its coenzyme, flavin-adenine dinucleotide), an amount of hydrogen peroxide corresponding to the amount of D-alanine being formed at the same time. This hydrogen peroxide is, in turn, used to oxidize o-dianisidine with the aid of a peroxidase. Since the amount of oxidized o-dianisidine thus formed is closely dependent on the amount of D-alanine and since the oxidized o-dianisidine produces a coloration, measurement of the intensity of the color thus produced can be utilized to determine the amount of D-alanine by a colorimetric method of determination.

It is obvious that this system is essentially based on the use of a substance, in this case o-dianisidine, the oxidized and the reduced forms of which have different colors. Substances of this type are known as redox indicators.

There is a large number of redox indicators which can usefully replace the o-dianisidine in the above-mentioned method. Examples which may be mentioned include the ammonium salt of 2,2'-azinobis(3-ethyl-2,3-dihydro-6-benzothiazolesulfonic) acid, 4-amino-antipyrine in the presence of phenol or of N,N-dimethylaniline and the like.

It is for this reason that, according to a preferred embodiment, the amount of D-alanine is determined by incubating the mixture of step (3), on the one hand, with a D-amino acid oxidase, which catalyzes the oxidation of the D-alanine to pyruvic acid (with the simultaneous formation of hydrogen peroxide) and, on the other hand, with a peroxidase and a redox indicator, the latter being oxidized by the hydrogen peroxide formed, by means of the peroxidase, to produce a coloration the intensity of which is a function of the amount of D-alanine.

The coenzyme of the D-amino acid oxidase, flavin-adenine dinucleotide (FAD), is of course always used in conjunction with the D-amino acid oxidase.

In this preferred embodiment, it is possible, in principle, to employ any redox indicator which is capable of being oxidized by hydrogen peroxide, in the presence of peroxidase as a catalyst. Particularly preferred redox indicators include o-dianisidine, the oxidized form of which has a brown coloration (maximum absorption at $\lambda = 460$ nm), and the ammonium salt of 2,2'-azinobis(3-ethyl-2,3-dihydro-6-benzothiazolesulfonic) acid, the oxidized form of which has a green coloration (maximum absorption at $\lambda = 420$ nm).

It will be noted that the brown coloration of oxidized o-dianisidine can advantageously be changed to a bright pink coloration by adding sulfuric acid. This pink coloration is very stable and this is very important if it is desired to keep the result of the determination for a certain time.

Furthermore, in order to ensure a rapid determination, it is possible to conduct step (3) and (4) simultaneously. In this embodiment, the reagents which make it possible to determine the D-alanine are added directly, at step (3) of the process, to the mixture of the immobilized enzyme and the substrate solution and a single incubation of the whole is carried out under conditions substantially identical to those indicated above for step (3).

In step (5) of the process, the determination of step (4) is compared with a standard in order to obtain the concentration of the antibiotic in the biological liquid.

The quantitative determination of the concentration of antibiotic can be carried out according to the following method:

First, a series of samples of the biological liquid, containing a known concentration of beta-lactam antibiotic, are prepared.

In addition to a certain number of samples containing an increasing concentration of antibiotic, this series will include two samples of the biological liquid which do not contain antibiotic.

All these samples are then treated in a strictly identical manner by following steps (1), (2), (3) and (4) of the process according to the present invention.

For one of the samples not containing antibiotic, however, the substrate solution used in step (3) is replaced by an identical volume of water. In this particular case, a solution which contains all the reagents except for the substrate will, therefore, be obtained at the end of stage (4). In view of the absence of the substrate, no D-alanine will, therefore, be formed and, consequently, the o-dianisidine will not be oxidized. The solution obtained will have a light yellow coloration. This sample is referred to hereinafter as the "blank sample".

In contradistinction thereto, the other sample not containing antibiotic produces a pronounced brown coloration. Indeed, since the sample does not contain antibiotic, the enzyme R 39 is not inactivated in step (1) and a maximum amount of D-alanine (corresponding to the total activity of the enzyme R 39 used) and hence a maximum amount of oxidized o-dianisidine will be formed and, consequently, a pronounced brown coloration will be produced. This sample is referred to hereinafter as the "control sample".

It will also be understood that if the samples contain a molar amount of antibiotic which is less than the molar amount of enzyme R 39 used, only a fraction of this enzyme will be inactivated by the antibiotic in step (1); in these cases, an amount of D-alanine corresponding to the (residual) activity of the fraction of the enzyme which has not been inactivated by the antibiotic, and consequently also a corresponding amount of oxidized o-dianisidine, will, therefore, be formed. In these cases, a brown coloration will, therefore, again be produced but its intensity will be less than that observed with the control sample.

Finally, if the samples contain a molar amount of antibiotic which is equal to or greater than the molar amount of enzyme R 39 used, the enzyme will be completely inactivated by the antibiotic during step (1); no D-alanine will, therefore, be formed and the o-dianisidine will not be oxidized. In these cases, a light yellow coloration identical to that observed with the blank sample will, therefore, be obtained.

In order to obtain an accurate determination, the optical density of the colorations obtained respectively with all the samples, including the blank and control samples, is measured on a spectrophotometer.

As a certain optical density value is also found for the blank sample, it is necessary to substrate this value from those found respectively for the control sample and for the other samples.

Starting from the optical density values thus obtained, the percentage residual activity (of the enzyme R 39) is calculated for each sample. This percentage is equal to the ratio, multiplied by 100, of the optical density value found for the sample in question to the optical density value found for the control sample.

A graph is then plotted with the concentration of antibiotic on the abscissa and the percentage residual activity of the enzyme R 39 on the ordinate.

A straight line is obtained which respectively intersects with the ordinate at a point corresponding to the control sample (100% of residual enzymatic activity) and with the abscissa at a point corresponding to the sample containing an amount of antibiotic equal to the molar amount of enzyme R 39 used (0% of residual enzymatic activity).

The graph thus obtained constitutes a "standard curve" which makes it possible to determine an unknown concentration of beta-lactam antibiotic in a sample of the biological liquid used to plot the graph. For this purpose, this sample is treated in a strictly identical manner by following steps (1), (2), (3) and (4) of the process according to the present invention; the optical density of the coloration obtained is measured on a spectrophotometer; the optical density value found for the blank sample is subtracted therefrom; the percentage residual enzymatic activity is calculated in the manner indicated above and the antibiotic concentration of the sample is obtained by referring to the standard curve.

It is thus possible to determine quantitatively antibiotic concentrations as low as 0.0005 I.U./ml of biological liquid in a little less than one hour.

This method requires the use of a spectrophotometer and, in principle, must, therefore, be carried out in a laboratory. However, if it is intended solely to determine whether or not the concentration of antibiotic exceeds a certain threshold (for example a maximum concentration established by the dairy industry), it is not necessary to use a spectrophotometer. This method requires some prior explanation.

As seen above, the standard curve intersects with the abscissa at a point corresponding to a sample containing an amount of antibiotic equal to the molar amount of enzyme R 39 used. At this critical concentration, the percentage residual enzymatic activity is zero % because, at the end of step (4) of the process according to the present invention, a light yellow coloration is obtained which is identical to that obtained with the blank sample.

A light yellow coloration is also obtained above this critical concentration because the percentage residual enzymatic activity is still zero %. Conversely, below this critical concentration, a brown coloration is obtained because a certain percentage residual enzymatic activity remains.

Consequently, simply on the basis of the coloration observed at the end of step (4) of the process, it is possible to evaluate directly in a sample whether or not the antibiotic concentration exceeds the critical concentration.

Therefore, it suffices to know the critical concentration so that it is then possible, without using a spectrophotometer, rapidly to determine if a sample contains a concentration of beta-lactam antibiotic which does (or does not) exceed this critical concentration. For this purpose, this sample is treated in an identical manner according to step (1), (2), (3) and (4) of the process according to the present invention and the coloration obtained is then simply observed; if this coloration is light yellow, the concentration of antibiotic will be at least equal to the critical concentration; on the other hand, if it is brown, the concentration of antibiotic will be lower than the critical concentration.

It is thus possible to determine, visually and with certainty, whether samples contain more or less than 0.002 I.U. of antibiotic per ml of biological liquid and to do this in a time of less than one hour.

This method is, therefore, perfectly suitable for examination of a series of milk samples, even outside the laboratory, for example on site at the farm, by unskilled personnel.

The method according to the present invention for the quantitative and qualitative determination of the antibiotic concentration has now been explained in detail with reference more particularly to the color change produced by o-dianisidine. However, those skilled in the art will easily understand that, when using other redox indicators in this method, only the color observed will be different.

A further object of the present invention is to provide a test set which can be used for carrying out the process according to the present invention, i.e. which can be used for the determination of a beta-lactam antibiotic in a biological liquid.

This test set comprises, in particular:
(1) a definite amount of soluble D-alanyl-D-alanine-carboxypeptidase produced by Actinomadura R 39, said enzyme being immobilized on a water-insoluble support;
(2) a definite amount of substrate;
(3) reagents allowing the determination of D-alanine; and (4) if appropriate, a standard with which the results of tests carried out with reagents of (1), (2) and (3) may be compared.

According to a preferred embodiment, the enzyme R 39 is immobilized on a cross-linked poly(N,N-dimethylacrylamide) resin, the substrate is the tripeptide $N^{alpha}$, $N^{epsilon}$-diacetyl-L-lysyl-D-alanyl-D-alanine or $N^{alpha}$-acetyl-L-lysyl-D-alanyl-D-alanine and the reagents comprise (a) a D-amino acid oxidase (in conjunction with its coenzyme, flavin-adenine dinucleotide), (b) a peroxidase and (c) a redox indicator, for example o-dianisidine or the ammonium salt of 2,2'-azinobis(3-ethyl-2,3-dihydro-6-benzothiazolesulfonic) acid.

As the standard, a standard curve of the antibiotic concentration versus the percentage residual activity of the enzyme R 39 can be included in the test set, if appropriate. It is thus possible to carry out quantitative determinations as explained above. However, this graph is not essential. In fact, if the test set is to be used solely to determine whether or not the concentration of antibiotic exceeds a certain critical value, it suffices to indicate, in the directions for use, the concentrations of antibiotic at which a change in the coloration is observed after the sample has been treated by the process according to the present invention.

According to a particularly advantageous embodiment, the immobilized enzyme is placed in a syringe which is fitted on the bottom with a plate of filtering material, for example sintered glass. This device facilitates the separation of the immobilized enzyme R 39 from the biological liquid by filtration and the washing of the enzyme in step (2) of the process according to the invention.

The following Examples are given for the purpose of illustrating the present invention:

EXAMPLE 1

This Example illustrates the application of the process according to the present invention to the determination of low concentrations of penicillin G in milk.

(a) Preparation of the reagents (1) Immobilized enzyme R 39.

The enzyme R 39 has been immobilized on a poly(N,N-dimethylacrylamide) resin according to the method described in the example previously given in the description.

(2) Substrate solution.

A solution containing 6 mg of $N^{alpha}$, $N^{epsilon}$-diacetyl-L-lysyl-D-alanyl-D-alanine in 1 ml of water is prepared.

(3) D-amino acid oxidase suspensions.

A suspension containing 5 mg of D-amino acid oxidase (specific activity: 15 U/mg) per ml of a 3 molar aqueous solution of ammonium sulfate is prepared.

(4) Flavin-adenine dinucleotide (FAD) solution.

A solution containing 500 µg of FAD in 6 ml of 0.1M Tris-HCl buffer (pH: 8.0) is prepared (M=mole per liter).

(5) Peroxidase solution.

A solution containing 50 µg of peroxidase per ml of water is prepared.

(6) o-Dianisidine solution.

A solution containing 2.6 mg of o-dianisidine dihydrochloride per 500 µl of water is prepared.

(b) Procedure

A series of 1 ml milk samples each containing a known concentration of penicillin G and two 1 ml milk samples (blank and control) not containing penicillin G are prepared.

5.5 mg of immobilized enzyme R 39 (=3 picomols of enzyme) are added to each sample and the mixture is incubated for 20 minutes at 37° C.

The milk is then separated from the immobilized enzyme by filtration and the immobilized enzyme is washed three times with 1 ml of 0.1M Hepes buffer (pH=7.7) containing 0.1M NaCl and 0.05M $MgCl_2$.

Either 20 µl of 0.1M Hepes buffer (pH=7.7) containing 0.1M NaCl and 0.05M $MgCl_2$ and 10 µl of the substrate solution (in the case of the control sample and the samples containing penicillin G), or 20 µl of the Hepes buffer and 10 µl of water (in the case of the blank sample), are then added to the separated and washed immobilized enzyme. The mixture is incubated for 30 minutes at 37° C.

At the end of this incubation, 2 µl of the D-amino acid oxidase suspension, 60 µl of the FAD solution, 10 µl of the peroxidase solution and 5 µl of the o-dianisidine solution are added respectively to the product obtained; the mixture is then incubated again for 10 minutes at 37° C.

The optical density of the colored solutions obtained is then measured on a spectrophotometer. For this purpose, 1 ml of a methanol/water solution (proportions 1:1) is added to the cell and the optical density is measured at 460 nm.

The optical density value found for the blank sample is subtracted from the optical density values found respectively for the control sample and for the other samples. Finally, the percentage residual enzymatic activity is calculated for each sample from the optical density values thus obtained.

The results obtained with two series of 1 ml milk samples containing varying concentrations of penicillin G are given in the following Table I:

TABLE I

| A | B | C | Δ | % | D |
|---|---|---|---|---|---|
| 1st series | | | | | |
| 1 | 0.0082 | 0.035 | 0.000 | 0 | light yellow |
| 2 | 0.0041 | 0.040 | 0.005 | 3 | light yellow |
| 3 | 0.0020 | 0.035 | 0.000 | 0 | light yellow |
| 4 | 0.0010 | 0.150 | 0.115 | 69 | yellow-brown |
| 5 | 0.0005 | 0.170 | 0.135 | 82 | brown |
| control | 0 | 0.200 | 0.165 | 100 | brown |
| blank | 0 | 0.035 | — | — | light yellow |
| 2nd series | | | | | |
| 1 | 0.0020 | 0.040 | 0.005 | 3 | light yellow |
| 2 | 0.0015 | 0.055 | 0.020 | 12 | yellow |
| 3 | 0.0010 | 0.100 | 0.065 | 41 | yellow-brown |
| 4 | 0.0005 | 0.145 | 0.110 | 69 | yellow-brown |
| control | 0 | 0.195 | 0.160 | 100 | brown |
| blank | 0 | 0.035 | — | — | light yellow |

A = sample number;
B = concentration of penicillin G (I.U./ml);
C = optical density at 460 nm;
Δ = optical density found (column 3) - optical density of the blank sample;
% = percentage residual enzymatic activity;
D = coloration observed.

The results thus obtained are reproduced in the form of a graph, which is illustrated on the accompanying drawing. On this graph, the concentration of penicillin G in I.U./ml has been plotted on the abscissa and the percentage residual enzymatic activity (symbol %) has been plotted on the ordinate.

This graph constitutes a standard curve which makes it possible to determine the concentration of penicillin G in other 1 ml milk samples. For this purpose, these samples are treated in the manner described in this Example and the respective concentrations of penicillin G therein are determined by referring to the standard curve.

Table I shows that, for a sample containing 0.002 I.U. or more of penicillin per ml of milk, a residual enzymatic activity of the order of zero % is found and a light yellow coloration is observed which is identical to that of the blank sample. On the other hand, for the samples containing an amount of less than 0.002 I.U. of penicillin per ml of milk, a certain percentage residual enzymatic activity is found and a yellow-brown or brown coloration is observed.

Consequently, simply on the basis of the coloration observed at the end of the final incubation, it is possible to determine, visually and with certainty, whether a milk sample contains a concentration equal to at least 0.002 I.U. of penicillin per ml of milk, i.e. 1.2 ng/ml of milk. In fact, at this concentration or at a higher concentration, a light yellow coloration is obtained which is identical to that of the blank sample. Conversely, below this concentration (for example if the sample does not contain penicillin), the coloration changes from light yellow to brown.

It is, therefore, apparent that the process according to the present invention makes it possible to carry out very rapidly a determination of very low concentrations of penicillin in milk, without having to use a spectrophotometer or other similar analytical instrument. This shows the great utility of this process, which makes it possible to carry out rapid determinations on a series of milk samples, at the actual location where the milk is collected, for example at the farm by untrained personnel.

Furthermore, it is obvious that this process can also be used for carrying out quantitative determinations in the laboratory. The graph illustrated in the accompanying drawing clearly shows that it is possible, by using a spectrophotometer, to determine concentrations as low as 0.0005 I.U. of penicillin per ml of milk, i.e. 0.3 ng/ml of milk.

EXAMPLE 2

This Example illustrates the application of the process according to the invention for the determination of low concentrations of penicillin G in serum and urine.

The procedure of Example 1 is followed, using the same reagents but replacing the 1 ml milk samples by 1 ml serum or 1 ml urine samples.

The results obtained are given in the following Tables II and III for serum and urine respectively:

TABLE II

| | | (serum) | | | |
|---|---|---|---|---|---|
| A | B | C | Δ | % | D |
| 1 | 0.010 | 0.030 | 0.000 | 0 | light yellow |
| 2 | 0.003 | 0.035 | 0.005 | 4 | light yellow |
| control | 0 | 0.145 | 0.115 | 100 | brown |
| blank | 0 | 0.030 | — | — | light yellow |

TABLE III

| | | (urine) | | | |
|---|---|---|---|---|---|
| A | B | C | Δ | % | D |
| 1 | 0.010 | 0.035 | 0.005 | 4 | light yellow |
| 2 | 0.003 | 0.040 | 0.010 | 8 | light yellow |
| control | 0 | 0.150 | 0.120 | 100 | brown |
| blank | 0 | 0.030 | — | — | light yellow |

Tables II and III clearly show that the process according to the invention can be successfully used to determine visually whether a sample of serum or urine contains a concentration of at least 0.003 I.U. of penicillin per ml of serum or urine.

Indeed, at this concentration or at a higher concentration, the observed coloration will be light yellow.

It should be noted that in the case of urine, it is impossible to carry out such a determination by the J-M. FRERE process, in which soluble non-immobilized enzyme R 39 is used and this is even the case for urine volumes which are as low as 10 μl.

EXAMPLE 3

This Example illustrates the application of the process according to the invention for the dosage of cephalosporin C in serum.

The procedure of Example 1 is followed, using the same reagents but replacing the 1 ml milk samples by 1 ml serum samples containing each a known concentration of cephalosporin C.

The results obtained are given in the following Table IV:

TABLE IV

| A | B* | C | Δ | % | D |
|---|---|---|---|---|---|
| 1 | 10 | 0.030 | 0.000 | 0 | light yellow |
| 2 | 2 | 0.040 | 0.010 | 8 | light yellow |
| 3 | 1 | 0.085 | 0.055 | 44 | light yellow |
| control | 0 | 0.155 | 0.125 | 100 | brown |
| blank | 0 | 0.030 | — | — | light yellow |

*B = cephalosporin C concentration (ng/ml).

EXAMPLE 4

This Example illustrates the application of the process according to the invention for the dosage of cephalosporin C in serum, carried out at a higher temperature.

The procedure of Example 3 is followed but each incubation is carried out at 47° C. and at half the time.

Moreover, to each ml sample of serum, there is previously added 100 μl of 0.5M (pH 7.7) Hepes buffer containing 0.5M NaCl and 0.25M $MgCl_2$.

The results obtained are given in the following Table V:

TABLE V

| A | B* | C | Δ | % | D |
|---|---|---|---|---|---|
| 1 | 10 | 0.040 | 0.005 | 0 | light yellow |
| 2 | 2 | 0.035 | 0.000 | 0 | light yellow |
| 3 | 1 | 0.095 | 0.060 | 41 | light brown |
| control | 0 | 0.180 | 0.145 | 100 | brown |
| blank | 0 | 0.035 | — | — | light yellow |

*B = cephalosporin C concentration (ng/ml)

This Example clearly shows that on increasing the incubation temperature it is possible to considerably cut down the time required to conduct the process.

What is claimed is:

1. An enzymatic process for the determination of a beta-lactam antibiotic in a biological liquid which comprises the steps of:
  (1) incubating the liquid with the soluble D-alanyl-D-alanine-carboxypeptidase produced by Actinomadura R 39, said enzyme being immobilized on a water-insoluble support, said incubation being conducted under conditions allowing the beta-lactam antibiotic, if present in said liquid, to react with the enzyme to form an inactive and substantially irreversible equimolecular enzyme-antibiotic complex;
  (2) separating the immobilized enzyme from the liquid and washing it;
  (3) incubating the immobilized enzyme of step (2) with a substrate solution under conditions allowing the substrate to be hydrolyzed by the enzyme to form an amount of D-alanine corresponding to the residual enzymatic activity;
  (4) determining the amount of D-alanine formed in step (3); and
  (5) comparing the determination of step (4) with a standard to obtain the concentration of the antibiotic in the biological liquid.

2. The process of claim 1, wherein the water-insoluble support is a cross-linked poly(N,N-dimethylacrylamide) resin.

3. The process of claim 2, wherein the immobilization is effected by attaching the enzyme to the poly(N,N-dimethylacrylamide) resin by covalent bonding.

4. The process of claim 1, wherein steps (3) and (4) are conducted simultaneously.

5. The process of claim 1, wherein the biological liquid is selected from the group consisting of milk, serum, urine, blood, saliva, meat extracts and fermentation liquids.

6. The process of claim 1, wherein the antibiotic to be determined is selected from the group consisting of benzylpenicillin, ampicillin, phenoxymethylpenicillin, carbenicillin, methicillin, oxacillin, cloxacillin, cephalosporin C, cephaloglycin, cephalothin and cephalexin.

7. The process of claim 1, wherein the substrate is $N^{alpha}$, $N^{epsilon}$-diacetyl-L-lysyl-D-alanyl-D-alanine or $N^{alpha}$-acetyl-L-lysyl-D-alanyl-D-alanine.

8. The process of claim 1, wherein the amount of D-alanine is determined by incubating the mixture of step (3), on the one hand, with a D-amino acid oxidase, which catalyzes the oxidation of the D-alanine to pyruvic acid with the simultaneous formation of hydrogen peroxide and, on the other hand, with a peroxidase and a redox indicator, the latter being oxidized by the hydrogen peroxide formed, by means of the peroxidase, to produce a coloration, the intensity of which is a function of the amount of D-alanine.

9. The process of claim 8, wherein the redox indicator is o-dianisidine or the ammonium salt of 2,2-azinobis(3-ethyl-2,3-dihydro-6-benzothiazole-sulfonic) acid.

10. The process of claim 1, wherein said standard is a standard curve of antibiotic concentration versus percentage residual enzymatic activity.

11. A test set for the determination of a beta-lactam antibiotic in a biological liquid, said set comprising:
  (1) a definite amount of soluble D-alanyl-D-alanine-carboxypeptidase produced by Actinomadura R 39, said enzyme being immobilized on a water-insoluble support;
  (2) a definite amount of substrate; and
  (3) reagents allowing the determination of D-alanine.

12. The test set of claim 11, wherein the water-insoluble support is a cross-linked poly(N,N-dimethylacrylamide) resin.

13. The test set of claim 11, wherein the substrate is $N^{alpha}$, $N^{epsilon}$-diacetyl-L-lysyl-D-alanyl-D-alanine or $N^{alpha}$-acetyl-L-lysyl-D-alanyl-D-alanine.

14. The test set of claim 11, wherein the reagents of (3) comprise (a) a D-amino acid oxidase, (b) a peroxidase and (c) a redox indicator.

15. The test set of claim 14, wherein the redox indicator is o-dianisidine or the ammonium salt of 2,2'-azinobis(3-ethyl-2,3-dihydro-6-benzothiazole-sulfonic) acid.

16. A test set for the determination of a beta-lactam antibiotic in a biological liquid, said set comprising:
  (1) a definite amount of soluble D-alanyl-D-alanine-carboxypeptidase produced by Actinomadura R 39, said enzyme being immobilized on a water-insoluble support;
  (2) a definite amount of substrate;
  (3) reagents allowing the determination of D-alanine; and
  (4) a standard with which the results of tests carried out with the reagents of (1), (2) and (3) may be compared.

17. The test set of claim 16, wherein said standard is a standard curve of antibiotic concentration versus percentage residual enzymatic activity.

* * * * *